United States Patent
Millet Aguilar-Galindo et al.

(10) Patent No.: US 11,337,966 B2
(45) Date of Patent: May 24, 2022

(54) USE OF CICLOPIROX AS A MODULATOR OF THE HEME GROUP BIOSYNTHESIS AND IN THE TREATMENT OF PORPHYRIAS AND OTHER DISEASES

(71) Applicant: ASOCIACIÓN CENTRO DE INVESTIGACIÓN COOPERATIVA EN BIOCIENCIAS-CIC bioGUNE, Derio-Vizcaya (ES)

(72) Inventors: Oscar Millet Aguilar-Galindo, Derio-Vizcaya (ES); Arantza Sanz Parra, Derio-Vizcaya (ES); Ana Laín Torre, Derio-Vizcaya (ES); Pedro David Urquiza Ortiz, Derio-Vizcaya (ES); Juan Manuel Falcón Pérez, Derio-Vizcaya (ES); Joaquín Castilla Castrillón, Derio-Vizcaya (ES); Itxaso San Juan Quintana, Derio-Vizcaya (ES); Ganeko Bernardo-Seisdedos, Derio-Vizcaya (ES)

(73) Assignee: ASOCIACIÓN CENTRO DE INVESTIGACIÓN COOPERATIVA EN BIOCIENCIAS-CIC BIOGUNE, Derio-Vizcaya (ES)

( * ) Notice: Subject to any disclaimer, the term of this patent is extended or adjusted under 35 U.S.C. 154(b) by 229 days.

(21) Appl. No.: 16/614,873

(22) PCT Filed: Apr. 27, 2018

(86) PCT No.: PCT/EP2018/060847
§ 371 (c)(1),
(2) Date: Nov. 19, 2019

(87) PCT Pub. No.: WO2018/233914
PCT Pub. Date: Dec. 27, 2018

(65) Prior Publication Data
US 2020/0171013 A1    Jun. 4, 2020

(30) Foreign Application Priority Data
Jun. 19, 2017    (EP) .................................... 17382371

(51) Int. Cl.
*A61K 31/4418*    (2006.01)
*A61P 7/00*    (2006.01)
*A61K 9/00*    (2006.01)
*A61K 9/06*    (2006.01)

(52) U.S. Cl.
CPC ........ *A61K 31/4418* (2013.01); *A61K 9/0014* (2013.01); *A61K 9/0053* (2013.01); *A61K 9/06* (2013.01); *A61P 7/00* (2018.01)

(58) Field of Classification Search
None
See application file for complete search history.

(56) References Cited

U.S. PATENT DOCUMENTS

2013/0281511 A1    10/2013    Bettencourt et al.

FOREIGN PATENT DOCUMENTS

| WO | WO2012017088 A1 | 2/2012 |
| WO | WO2012174126 A1 | 12/2012 |

OTHER PUBLICATIONS

Bdira, F.B., et al., "Tuning Intracellular Homeostatis of Human Uroporphyrinogen III Synthase by Enzyme Engineering at a Single Hotspot of Congenital Erythropoietic Porphyria", "Human Molecular Genetics", 2014, pp. 5805-5813, vol. 23, No. 21.
Blouin, J., et al., "Therapeutic Potential of Proteasome Inhibitors in Congenital Erythropoietic Porphyria", "PNAS", 2013, pp. 18238-18243, vol. 110, No. 45.
Di Pierro, E., et al., "Advances in Understanding the Pathogenesis of Congenital Erythropoietic Porphyria", "British Journal of Haematology", 2016, pp. 365-379, vol. 173.
Egan, D., et al., "Inducing Iron Deficiency Improves Erythropoiesis and Photosensitivity in Congenital Erythropoietic Porphyria", "Blood", 2015, pp. 257-261, vol. 126, No. 2.
Fortian, A., et al., "Uroporphyrinogen III Synthase Mutations Related to Congenital Erythropoietic Porphyria Identify a Key Helix for Protein Stability", "Biochemistry", 2009, pp. 454-461, vol. 48.
Fortian, A., et al., "Intracellular Rescue of the Uroporphyrinogen III Synthase Activity in Enzymes Carrying the Hotspot Mutation C73R", "Journal of Biological Chemistry", Apr. 15, 2011, pp. 13127-13133, vol. 286, No. 15.
Minden, M.D., et al., "Oral Ciclopirox Olamine Displays Biological Activity in a Phase I Study in Patients with Advanced Hematologic Malignancies", "American Journal of Hematology", Apr. 4, 2014, pp. 363-368, vol. 89, No. 4.
Puy, H., et al., "Heme-Related Blood Disorders", "55th Annual Meeting of the American Chemical Society of Hematology", 2013, pp. 1-3, No. XP002776008.
Shoolingin-Jordan, P., et al., "Coupled Assay for Uroporphyrinogen III Synthase", "Methods in Enzymology", 1997, pp. 327-336, vol. 281.
Tauber, A., et al., "Comparison of the Antifungal Efficacy of Terbinafine Hydrochloride and Ciclopirox Olamine Containing Formulations Against the Dermatophyte Trichophyton Rubrum in an Infected Nail Plate Model", "Molecular Pharmaceutics", 2014, pp. 1991-1996, vol. 11.
Urquiza, P., et al., "New Pharmacological Therapies Against Congenital Erythropoietic Porphyria (CEP)", "Protein Science", 2015, pp. 64, vol. 24, No. Suppl. 1.
Urquiza, P. et al., "Repurposing Ciclopirox as a Pharmacological Chaperone in a Model of Congenital Erythropoietic Porphyria", "Sci. Transl. Med", Sep. 19, 2018, pp. 1-9, vol. 10, No. eaat7467.

*Primary Examiner* — Savitha M Rao
*Assistant Examiner* — Gregg Polansky
(74) *Attorney, Agent, or Firm* — Hultquist, PLLC; Steven J. Hultquist

(57) ABSTRACT

The present invention relates to the use of the compound ciclopirox or a pharmaceutically acceptable salt or solvate thereof for the treatment and/or prevention of a disease caused by dysregulated heme group biosynthesis, with the proviso that said disease is not congenital erythropoietic porphyria.

14 Claims, 5 Drawing Sheets

A

B

USE OF CICLOPIROX AS A MODULATOR OF THE HEME GROUP BIOSYNTHESIS AND IN THE TREATMENT OF PORPHYRIAS AND OTHER DISEASES

CROSS-REFERENCE TO RELATED APPLICATIONS

This application is a U.S. national phase under the provisions of 35 U.S.C. § 371 of International Patent Application No. PCT/EP18/60847 filed Apr. 27, 2018, which in turn claims priority of European Patent Application No. EP17382371.7 filed Jun. 19, 2017. The disclosures of such International Patent Application No. PCT/EP18/60847 and European Patent Application No. EP17382371.7 priority patent application are hereby incorporated herein by reference in their respective entireties, for all purposes.

FIELD OF THE INVENTION

The present invention relates how ciclopirox is able to modulate heme group biosynthesis and how this property can be used for the treatment and/or prevention of several diseases including acute intermittent porphyria (AIP), porphyria cutanea tarda (PCT), hereditary coproporphyria (HC), harderoporphyria (HP), variegate porphyria (VP) and sideroblastic anaemia (SA) and hereditary hyperbilirubinemia syndromes, among others.

BACKGROUND OF THE INVENTION

The group of pathologies produced by a lack of activity in some of the enzymes of the heme group biosynthesis is generically known as porphyria. Normally the loss of activity is produced by mutations in the amino acid sequence of said proteins and the type of porphyria depends on the specific enzyme causing the mutation. The heme group biosynthesis is shown in Scheme 1 indicating the enzymes involved in each stage of the pathway (above the reaction arrow, including the four letter acronym) and detailing the names of the specific pathologies caused by functioning deficiencies in each of these enzymes (in italic form).

Porphyria patients can suffer from many symptoms depending on the specific pathology and the involved damaged enzyme. The porphyrias can be divided into erythropoietic and hepatic types, depending on where damaging compounds called porphyrins and porphyrin precursors first build up in the body (Table 1). In erythropoietic porphyrias, these compounds originate in the bone marrow. Erythropoietic porphyrias include erythropoietic protoporphyria and congenital erythropoietic porphyria (CEP). Health problems associated with erythropoietic porphyrias include a low number of red blood cells (anemia) and enlargement of the spleen (splenomegaly). The other types of porphyrias are considered hepatic porphyrias. In these disorders, porphyrins and porphyrin precursors originate primarily in the liver, leading to abnormal liver function and an increased risk of developing liver cancer (Table 1).

One common feature is the accumulation of the by-products: uroporphyrinogen I; UROgenI and coproporphyrinogen I; COPROgenI (Scheme I). Such products are easily oxidized to the respective porphyrins (UROI and COPROI) and they are difficult to catabolize by-products that tend to accumulate in the body. Thus, large amounts of UROgenI which accumulate in bags below the eyes and deform the extremities are produced in CEP patients (those having a UROS deficiency). By-product accumulation also results in an extreme sensitivity to sunlight from infancy that manifests as intense dermal lesions in the exposed areas. This is a common feature observed in several porphyrias, as described in Table 1.

Scheme 1: the heme biosynthetic pathway and its relationship with the porphyrias.

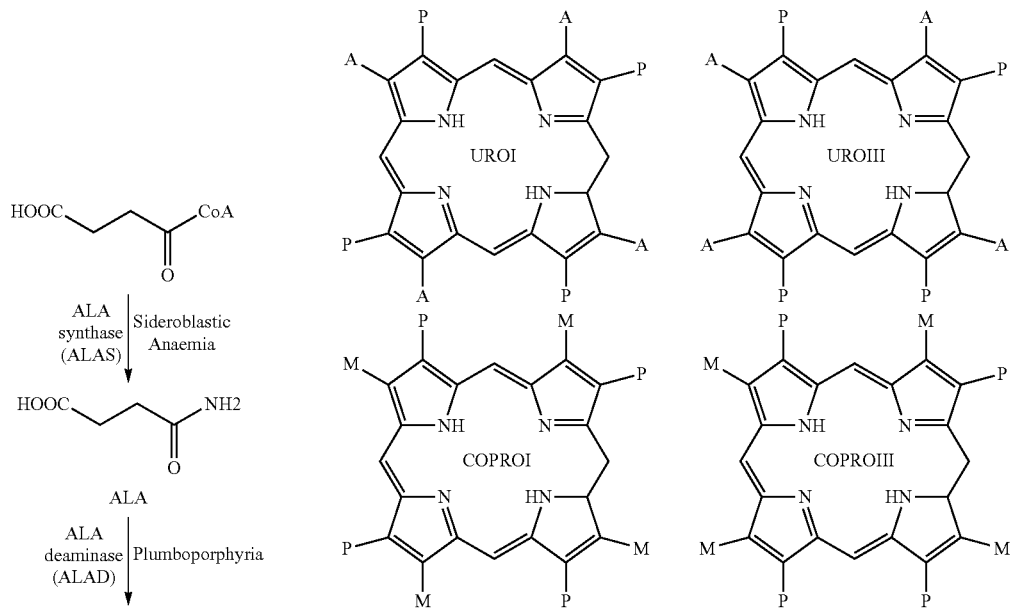

-continued

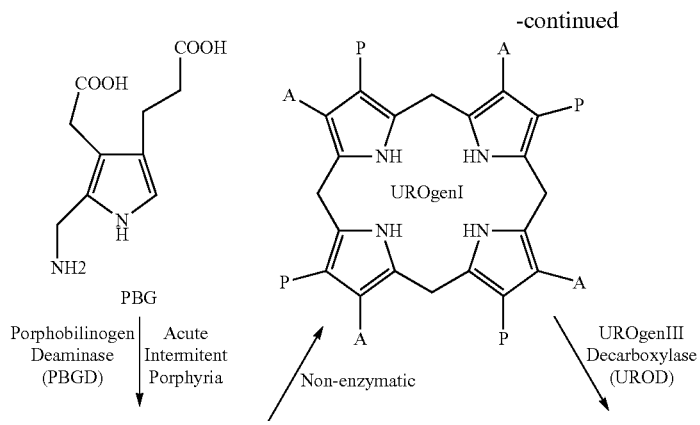

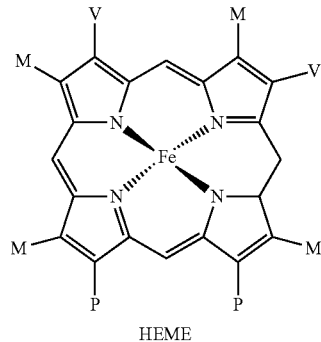

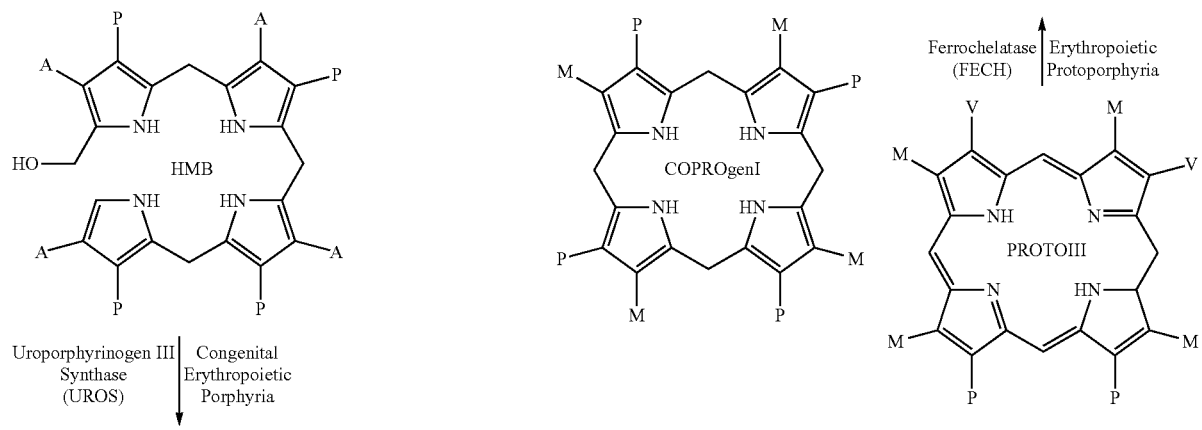

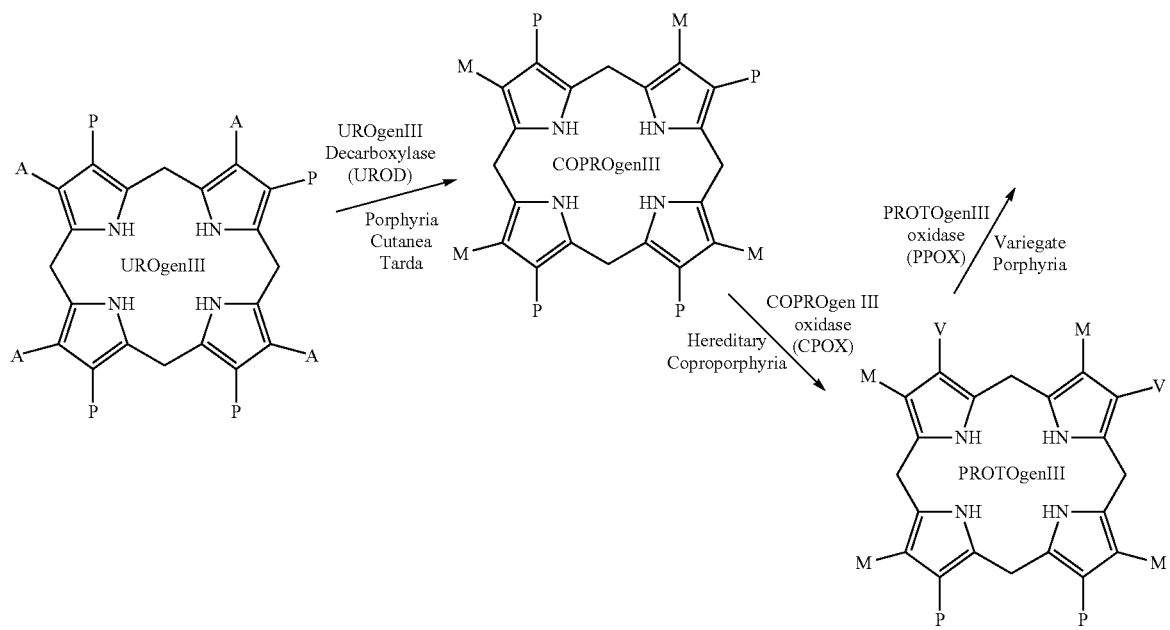

ALA: aminolevulinate
PBG: porphobilinogen
HMB: hydroxymethylbilane
PROTOgenIII: protoporphyrinogen
PROTOIII: protoporphyrin UROgenI: uroporphyrinogen I
UROI: uroporphyrin I
UROgenIII: uroporphyrinogen III
UROIII: uroporphyrin III COPROgenI: coproporphyrinogen I
COPROI: coproporphyrin I
COPROgenIII: coproporphyrinogen III
COPROIII: coproporphyrin III

[P = propionate, A = acetate, V = vinyl, M = methyl].

The heme group biosynthesis is regulated in three points: i) $Fe^{2+}$ and ALA upregulate the route, while the accumulation of heme results in the opposite effect due to feedback downregulation. In this context, a reduced heme group synthesis due to the ill-functioning in one of the enzymes in the route results in the activation of the route, severing the accumulation of by-products in the body and the skin photosensitivity.

TABLE 1 the family of porphyrias and the main symptoms observed by the patients.

| Porphyria Type | Deficient enzyme | Type | Main symptoms |
| --- | --- | --- | --- |
| Sideroblastic anemia (X-linked dominant protoporphyria) | ALAS | Erythro. | Cirrhosis, photosensitivity |
| Aminolevulinate dehydratase deficientcy porphyria | ALAD | Hep. | Abdominal pain, neuropathy |
| Acute Intermitent Porphyria | PBGD | Hep. | Abdominal pain, neuropathy, psychiatric disorders, tachycardia |
| Congenital erythropoietic Porphyria | UROS | Erythro. | Severe photosensitivity, hemolitic anemia, blistering, splenomegaly |
| Porphyria Cutanea Tarda | UROD | Hep. | Photosensitivity with vesicles and bullae |
| Hereditary Coproporphyria | CPOX | Hep. | Photosensitivity, neurologic pain, colic. |
| Harderoporphyria | CPOX | Erythro. | Jaundice, anemia, enlarged liver and spleen, late photosensitivity. |
| Variegate Porphyria | PPOX | Hep. | Photosensitivity, neurologic symptoms, developmental delay |
| Erythropoietic protoporphyria | FECH | Erythro. | Photosensitivity with skin lesions. Gallstones, mild liver dysfunction |

Heme biosynthetic enzymes have been intensively studied in recent years. All of the genes involved have been cloned and the crystal structures of all of the enzymes have been determined. In this context, regulation of the gene expression of the pathway has been proposed as a promising approach for the management of porphyric disorders.

However, currently there is no cure for any of the porphyrias and all the treatments are palliative or preventive. In acute porphyrias, outbreaks of symptoms often require hospitalization and patients may be given medicine for pain, nausea, and vomiting. Hemin is the only heme therapy approved for use. Treatment of cutaneous porphyria depends on the specific type and the severity of the symptoms and includes regular blood removal (phlebotomies) to reduce the amount of iron in the liver, and low doses of the antimalarial drug chloroquine. Curative experimental techniques are limited to bone marrow transplant (for erythropoietic porphyrias) with the subsequent danger of infection. Gene therapy has been explored for Congenital erythropoietic porphyria (in animal models) and acute intermittent porphyria (in humans) with no significant improvement.

Dysregulation of heme group biosynthesis has been also found to play a role in other diseases such as hereditary hyperbilirubinemia syndromes including Crigler-Najjar syndrome, Lucey-Driscoll syndrome, Gilbert syndrome, Rotor syndrome and Dubin-Jondon syndrome. In all these cases high levels of bilirubin and/or biliverdin are found. Since bilirubin and biliverdin are metabolites obtained from the catabolysis of heme group, a regulation of the latter should also reduce the levels of the former.

Thus, there is still a great need of providing therapeutic agents suitable for the treatment and/or prevention of porphyrias and other diseases associated with dysregulated heme group biosynthesis.

SUMMARY OF THE INVENTION

Described herein is a novel treatment for porphyria, hyperbilirubinemia and other diseases in which a dysregulation of the heme group biosynthesis is involved. In particular, we have demonstrated that the compound ciclopirox is able to regulate the heme group biosynthesis not by well-known mechanisms like regulation of the gene expression of the pathway but instead by its association and stabilization of the heme group, reducing the biosynthetic pathway upregulation and, ultimately reducing the intracellular concentration levels of the toxic by-products as well as heme catabolic products, underscoring an unexpected new way of heme regulation.

Therefore, the present invention relates to ciclopirox or a pharmaceutically acceptable salt or solvate thereof for use in the treatment and/or prevention of a disease caused by dysregulated heme group biosynthesis and characterized by the accumulation of UROI, COPROI, bilirubin and/or biliverdin, with the proviso that said disease is not congenital erythropoietic porphyria.

A further aspect is a pharmaceutical composition for use in the treatment and/or prevention of a disease caused by dysregulated heme group biosynthesis and characterized by the accumulation of UROI, COPROI, bilirubin and/or biliverdin, with the proviso that said disease is not congenital erythropoietic porphyria, said composition comprising ciclopirox, or a pharmaceutically acceptable salt or solvate thereof, and a pharmaceutically acceptable excipient. According to a particular embodiment, said composition is for oral or topical administration.

Also is disclosed a method for the treatment and/or prevention of a disease caused by dysregulated heme group biosynthesis in a subject and characterized by the accumulation of UROI, COPROI, bilirubin and/or biliverdin, with the proviso that said disease is not congenital erythropoietic porphyria, said method comprising the administration of a therapeutically effective amount of ciclopirox, or a pharmaceutically acceptable salt or solvate thereof to said subject. In a preferred embodiment, said subject is a human being.

Diseases arising from dysregulated heme synthesis are known to the skilled person, including the pathologies contemplated by the present invention, i.e. those which are characterized by (or result in) the accumulation of by-products of the heme biosynthesis pathway or heme catabolic products, said products being selected from UROI, COPROI, bilirubin and/or biliverdin, In a particular embodiment of the present invention, the disease caused by dysregulated heme group biosynthesis is characterized by the accumulation of UROI and/or COPROI. More particularly, said disease characterized by the accumulation of UROI and/or COPROI is a porphyria selected from the group consisting of sideroblastic anaemia, porphyria cutanea tarda, hereditary coproporphyria, harderoporphyria, variegate porphyria and erythropoietic protoporphyria.

In another embodiment, the disease caused by dysregulated heme group biosynthesis is characterized by the accumulation of bilirubin and/or biliverdin. More particularly, said disease characterized by the accumulation of bilirubin and/or biliverdin is selected from the group consisting of Crigler-Najjar syndrome, Lucey-Driscoll syndrome, Gilbert syndrome, Rotor syndrome, Dubin-Johnson syndrome and other hereditary hyperbilirubinemias.

DETAILED DESCRIPTION OF THE INVENTION

Figure 1:
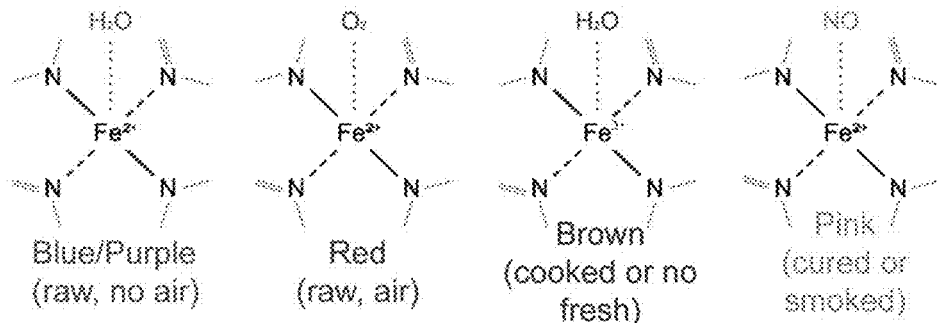
FIG. 1. The association of ciclopirox (CPX) to the heme group changes the absorption frequency and the color due to the different coordination properties of the non-covalent complex (A). The color of a heme solution changes progressively upon addition of CPX (B).
Figure 1:
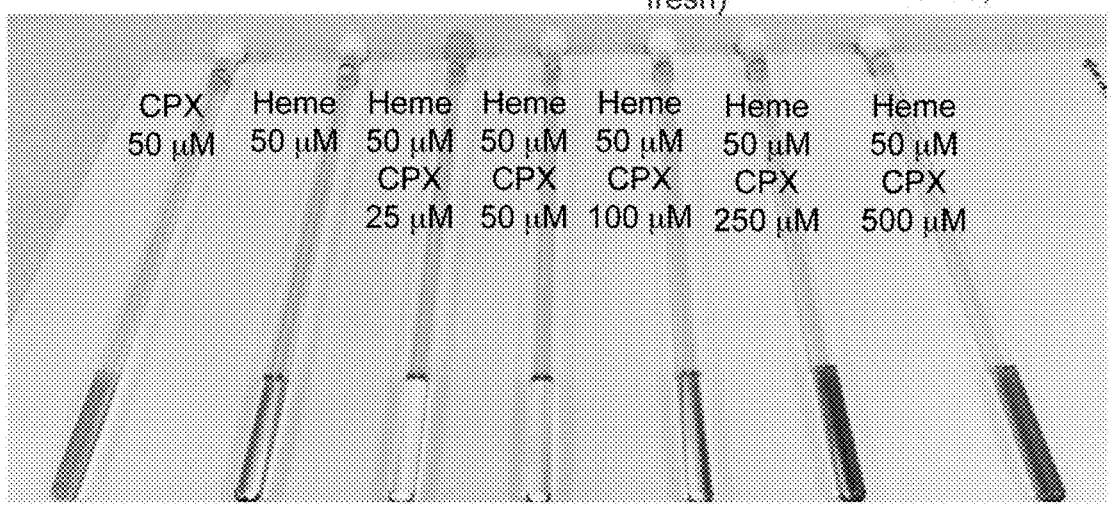

The compound ciclopirox was disclosed for the first time in the 1970s, in U.S. Pat. No. 3,883,545, where it was described as exhibiting antimycotic properties. The chemical name for ciclopirox is 6-cyclohexyl-1-hydroxy-4-methyl-2(1H)-pyridone, with the molecular formula $C_{12}H_{17}NO_2$ and a molecular weight of 207.27. The CAS Registry Number is [29342-05-0]. The chemical structure is depicted below in Scheme 2:

Scheme 2: ciclopirox

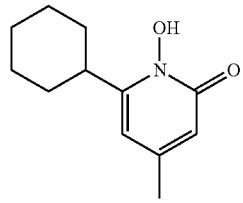

The present invention also contemplates all pharmaceutically acceptable salts and solvates of ciclopirox. For instance, ciclopirox can be for example ciclopirox olamine (CAS Registry Number [41621-49-2]), which comprises 6-cyclohexyl-1-hydroxy-4-methyl-2(1H)-pyridone with 2-aminoethanol in a 1:1 ratio.

Ciclopirox (and the salt ciclopirox olamine) have previously been described/used/approved as anti-fungal treatments. Currently, a variety of topical formulations indicated for the treatment of fungal infections are commercially available (e.g., as a lacquer, as a shampoo, as a solution, as a suspension, as a cream, as a lotion and as a gel).

Described herein is a new and surprising utility of the approved and commercially available drug ciclopirox. Specifically, in this invention it is demonstrated that ciclopirox is able to modulate the porphyrin concentration in several cellular models that accumulate porphyrins, ultimately resulting in a reduction of the generated toxic by-products. This is possible due to the fact that ciclopirox associates in a non-covalent way with the heme group (see example 1), thus stabilizing its concentration and activating the feedback regulation mechanism. This activity is reported at extracellular concentrations that are comparable to the dosage administered for the already approved medical uses, thus indicating that the compound may be active at concentration below the toxicity threshold. Further, the regulation of the heme biosynthesis pathway is also useful to decrease the levels of metabolites obtained from the catabolysis of heme group and therefore ciclopirox may be also beneficial in pathologies associated with the accumulation of heme catabolic products.

There has been to the inventor's knowledge no disclosure of the utility of ciclopirox (or salts) in the treatment of any disease by its ability to modulate the heme group biosynthesis as shown herein. Advantageously, the capacity of ciclopirox to non-covalently associate with the heme group and stabilize it represents a novel and effective mechanism for the treatment and/or prevention of diseases related to dysregulation of heme synthesis. The utility of ciclopirox in the treatment and/or prevention of congenital erythropoietic porphyria (CEP) due to its capacity to act as a pharmacological chaperone for uroporphyrinogen III synthase is the subject of the copending patent application PCT/EP2017/077570, filed on 27 Oct. 2017 and not published.

The present invention relates to the use of ciclopirox or a pharmaceutically acceptable salt or solvate thereof for the manufacture of a medicament for the treatment and/or prevention of diseases caused by dysregulated heme group biosynthesis, other than congenital erythropoietic porphyria. In a particular embodiment, the disease arises from the accumulation of UROI and/or COPROI and more particularly it is a porphyria selected from the group consisting of sideroblastic anaemia, porphyria cutanea tarda, hereditary coproporphyria, harderoporphyria, variegate porphyria and erythropoietic protoporphyria. In another embodiment, the disease is associated with the accumulation of bilirubin and/or biliverdin (catabolites of the heme group) such as Crigler-Najjar syndrome, Lucey-Driscoll syndrome, Gilbert syndrome, Rotor syndrome, Dubin-Johnson syndrome and other hereditary hyperbilirubinemias.

By "pharmaceutically acceptable" is meant herein a material that is not biologically or otherwise undesirable, i. e., the material may be incorporated into a pharmaceutical composition administered to a patient without causing any undesirable biological effects or interacting in a deleterious manner with any of the other components of the composition in which it is contained. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "salt" must be understood as any form of ciclopirox used according to this invention in which said compound is in ionic form or is charged and coupled to a counterion (a cation or anion).

Salts of ciclopirox may preferably be base addition salts or metallic salts, and they can be synthesized from the parent compound by conventional chemical methods. Examples of the alkali addition salts include inorganic salts such as, for example, ammonium, and organic alkali salts such as, for example, ethylenediamine, ethanolamine, triethanolamine, glucamine and basic aminoacids salts. Examples of the metallic salts include, for example, sodium, potassium, calcium, magnesium, aluminium and lithium salts. According to a particular embodiment, the salt of ciclopirox is a salt of alkali metals (for example of sodium or potassium); an ammonium salt; a primary amine salt (as for example $C_1$-$C_8$ alkyl amine); a secondary amine salt (as for example $C_1$-$C_8$ dialkyl amine); a tertiary amines salt (as for example $C_1$-$C_8$ trialkyl amine); a diamine salt; an alkanolamine salt (as for example $C_1$-$C_8$ alkanolamine or $C_1$-$C_8$ dialkanolamine or $C_1$-$C_8$ trialkanolamine); a $C_1$-$C_8$ dialkyl $C_1$-$C_8$ alkanolamine; or a $C_1$-$C_8$ alkyl $C_1$-$C_8$ dialkanolamine. A preferred ciclopirox salt is ciclopirox olamine.

The term "solvate" according to this invention is to be understood as meaning any form of the compound according to the invention in which this compound has attached to it via non-covalent binding another molecule (most likely a polar solvent) especially including hydrates and alcoholates, e.g. methanolate. Methods of solvation are generally known within the art.

According to an embodiment of the present invention, the compound ciclopirox or a pharmaceutically acceptable salt or solvate thereof is intended to modulate the heme biosynthetic pathway.

According to an embodiment of the present invention, the compound ciclopirox or a pharmaceutically acceptable salt or solvate thereof is intended to non-covalently associate with the heme group to stabilize it.

According to another embodiment of the present invention, the compound ciclopirox or a pharmaceutically acceptable salt or solvate thereof is intended to reduce the toxic porphyrin levels, in particular the levels of uroporphyrinogen (UROgenI), coproporphyrinogen I (COPROgenI) and/or their derivatives.

According to another embodiment of the present invention, the compound ciclopirox or a pharmaceutically acceptable salt or solvate thereof is intended to reduce the toxic levels of catabolites of the heme group, in particular the levels of bilirubin, biliverdin and/or their derivatives.

A further aspect is a pharmaceutical composition for use in the treatment and/or prevention of the abovementioned diseases comprising ciclopirox, or a pharmaceutically acceptable salt or solvate thereof, and a pharmaceutically acceptable excipient.

Examples of pharmaceutical compositions include any solid composition (e.g. tablets, pills, capsules, granules) or liquid composition (e.g. solutions, suspensions lotions or emulsions).

The compositions can for example be administered orally, topically, dermally, nasally, intravenously, intramuscularly, intraperitoneally, intracerobrospinally, intracranially, intraspinally, subcutaneously, intraarticularly, intrasynovially, or intrathecaly. Other forms of administration are not excluded. According to a particular embodiment, said composition is for oral or topical administration. According to another particular embodiment, said composition is formulated as a lacquer, as a shampoo, as a solution, as a suspension, as a cream, as a lotion or as a gel.

The respective composition may—depending on its route of administration—also contain one or more excipients known to those skilled in the art. The composition or medicament according to the present invention may be produced according to standard procedures known to those skilled in the art.

The term "excipient" refers to components of a drug compound other than the active ingredient (definition obtained from the European Medicines Agency—EMA). They preferably include a "carrier, adjuvant and/or vehicle". Carriers are forms to which substances are incorporated to improve the delivery and the effectiveness of drugs. Drug carriers are used in drug-delivery systems such as the controlled-release technology to prolong in vivo drug actions, decrease drug metabolism, and reduce drug toxicity. Carriers are also used in designs to increase the effectiveness of drug delivery to the target sites of pharmacological actions (U.S. National Library of Medicine. National Institutes of Health). Adjuvant is a substance added to a drug product formulation that affects the action of the active ingredient in a predictable way. Vehicle is an excipient or a substance, preferably without therapeutic action, used as a medium to give bulk for the administration of medicines (Stedman's Medical Spellchecker, © 2006 Lippincott Williams & Wilkins). Such pharmaceutical carriers, adjuvants or vehicles can be sterile liquids, such as water and oils, including those of petroleum, animal, vegetable or synthetic origin, such as peanut oil, soybean oil, mineral oil, sesame oil and the like, excipients, disgregants, wetting agents or diluents. Suitable pharmaceutical carriers are described in "Remington's Pharmaceutical Sciences" by E. W. Martin. The selection of these excipients and the amounts to be used will depend on the form of application of the pharmaceutical composition.

As used herein, the terms "treat", "treating" and "treatment" include in general the eradication, removal, reversion, alleviation, modification, or control of the abovementioned diseases after its onset.

As used herein, the terms "prevention", "preventing", "preventive", "prevent" and "prophylaxis" refer to the capacity of a given substance, composition or medicament to avoid, minimize or difficult the onset or development of the abovementioned diseases before its onset.

Also is disclosed a method of treatment of a patient, notably a human, suffering the abovementioned diseases, or likely to suffer the abovementioned diseases, which comprises administering to the patient in need of such a treatment or prophylaxis an effective amount of ciclopirox, or a pharmaceutically acceptable salt or solvate thereof.

By an "effective" amount or a "therapeutically effective amount" of a drug or pharmacologically active agent is meant a nontoxic but sufficient amount of the drug or agent to provide the desired effect. In the therapy of the present invention, an "effective amount" of ciclopirox or a pharmaceutically acceptable salt or solvate thereof is the amount of that compound that is effective to provide the desired effect. The amount that is "effective" will vary from subject to subject, depending on the age and general condition of the individual, the particular active agent or agents, and the like. Thus, it is not always possible to specify an exact "effective amount". However, an appropriate "effective" amount in any individual case may be determined by one of ordinary skill in the art using routine experimentation.

Ciclopirox can be used together with other additional useful drugs in the prevention and/or treatment of the abovementioned diseases. Said additional drugs can form part of the same pharmaceutical composition or, alternatively, can be provided in the form of a separated composition for their simultaneous or sequential administration to that of the pharmaceutical composition comprising ciclopirox or a pharmaceutically acceptable salt or solvate thereof. For example, the treatment with ciclopirox or a pharmaceutically acceptable salt or solvate thereof could be complimented with the administration of heme derivatives or blood products to counteract the heme group deficiency.

The following examples are provided as supporting evidence for the invention since they demonstrate that the compound ciclopirox is able to directly interact with heme and to reduce the toxic porphyrin levels in relevant cellular models that accumulate porphyrins and even in healthy cells. It has been also proved that the mechanism of action is not related to gene regulation.

EXAMPLES

1. Ciclopirox is Associated to Heme Group to Form a Coordination Complex.

Figure 2:
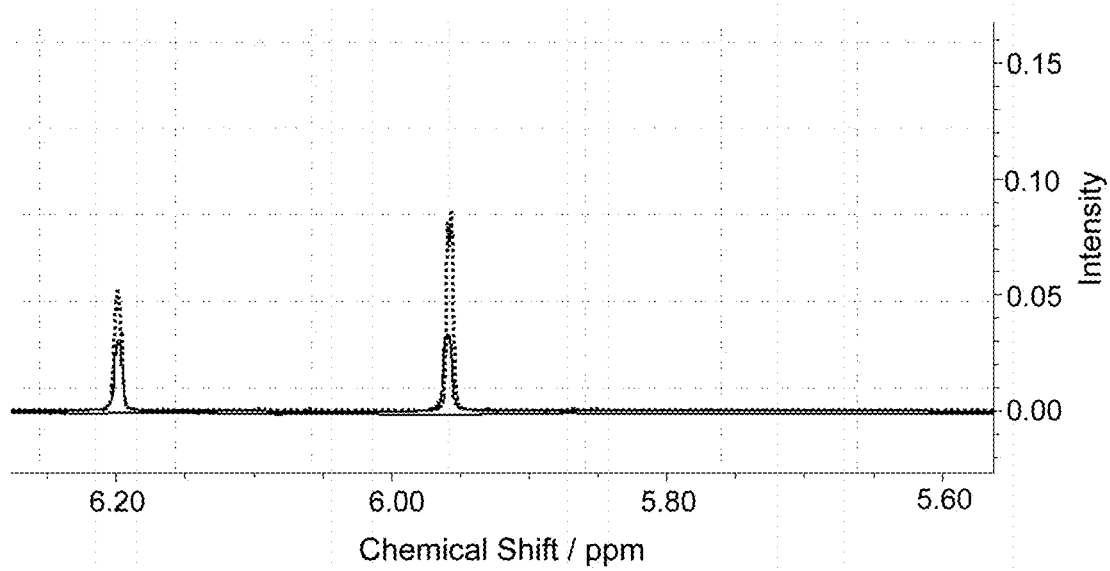
FIG. 2. The effect of the association can be observed by NMR. In the Figure is shown the aromatic region of the 1D $^1$H-NMR spectrum of CPX (dotted line). When one equivalent of heme is added to the sample, a reduction in the signal intensity is observed due to the association to heme and paramagnetic relaxation with the $Fe^{2+}$ ion (solid line).
Figure 3:
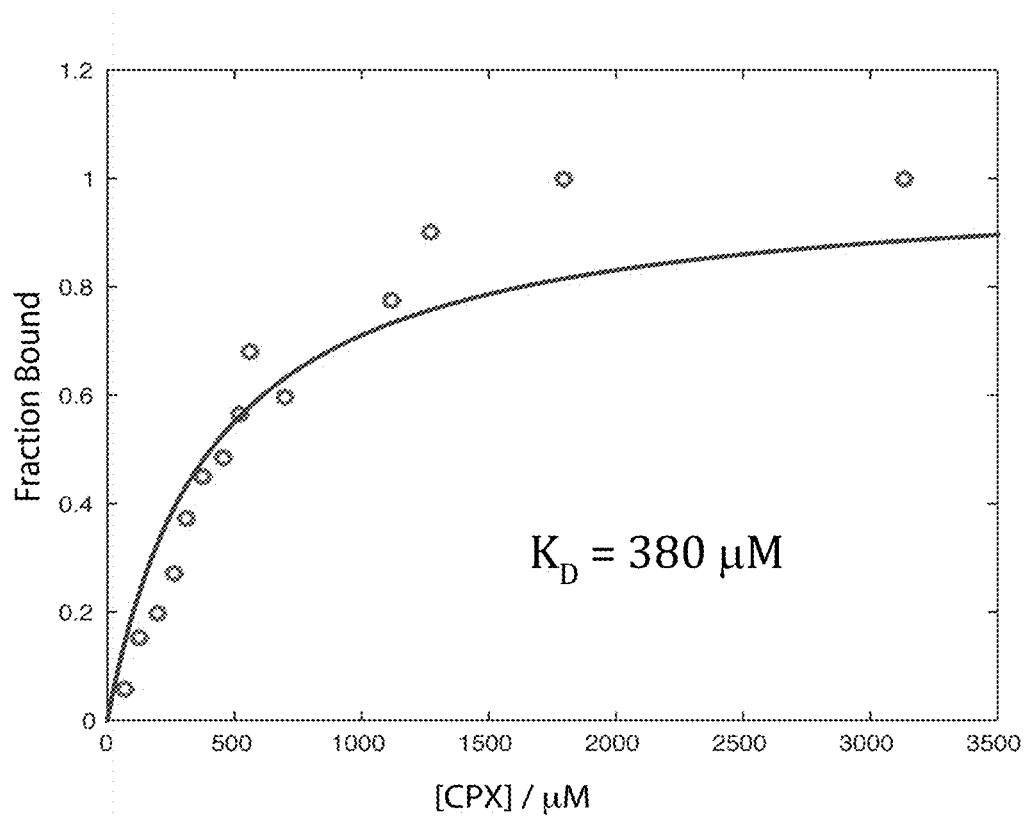
FIG. 3. The signal intensity change in the 1D $^1$H-NMR can be used to determine the affinity constant of the complex. The best fitting to the experimental data provides a value of 380 µM.

Ciclopirox interacts with heme group to form an octaedric coordination complex according to the change in color in a heme group sample in the presence of increasing amounts of CPX (FIG. 1). This change in color is a characteristic trait of the coordination geometry of the complex and it means that CPX does not compete with heme but stabilizes it. Further evidence of the interaction can be obtained from the paramagnetic linebroadening in the NMR signal induced by the $Fe^{2+}$ ion, as shown in FIG. 2. Actually, the quantification of this experiment repeated at different concentrations of CPX provides an estimation of the dissociation constant between CPX and the heme group (380 µM, FIG. 3).

Figure 4:
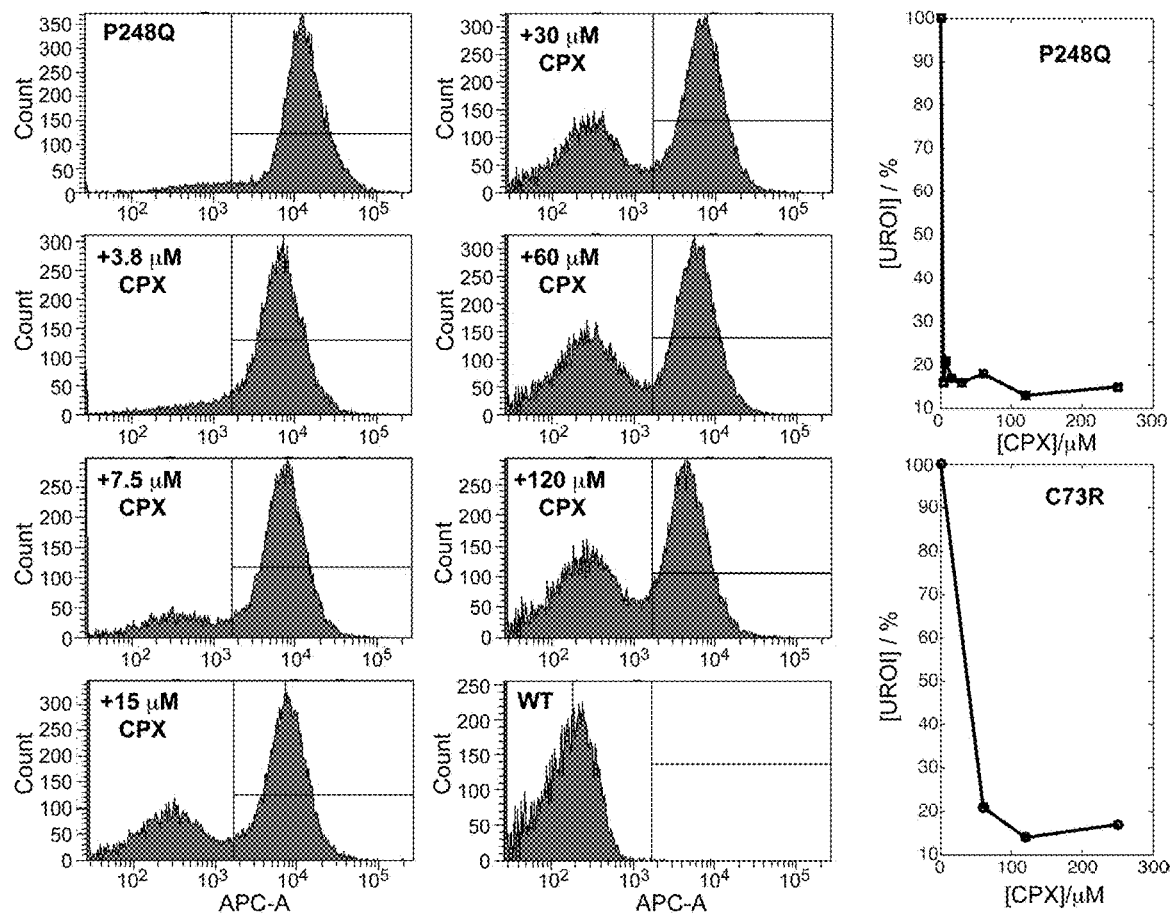
FIG. 4. Evaluation of Uroporphyrin I (UROI) levels in different HEK cell lines without porphyria phenotype (WT) or with an introduced genomic instability using CRISPR-cas9 technique (P248Q & C73R mutations). [Left] For the mentioned cell lines, the accumulation of porphyrins as a function of [CPX] is measured by fluorescence spectroscopy (fluorocytes) and is depicted in as the right-shift of the population as compared to normal cells (that are concentrated on the left due to the absence of intrinsic fluorescence). Side Scatter (SSC) and PE-Cy5 intensities are expressed in arbitrary units. [Right] The concentration of UROI as determined by HPLC analysis, as a function of the [CPX] for P248Q HEK [Top] and C73R HEK [Bottom] cell lines.

2. Ciclopirox Reduces UROI Levels in Cellular Models that Accumulate Porphyrins:

The current supporting data disclosed is in relation to a human in vitro cellular model of URO I porphyrin accumulation (obtained from HEK293 UROS-C73R cells) in which there is a stable genomic defect introduced into the uroporphyrinogen III synthase enzyme which drives the accumulation of toxic porphyrins. We have also demonstrated (Blouin et al. PNAS, 2013) that the tool compound MG in the human cellular model reduces toxic porphyrin levels supporting the observations from the in vivo model by FACS analysis of the cell lines (FIG. 4). The accumulation of porphyrins is measured by fluorescence spectroscopy (fluorocytes) and appear shifted to the right as compared to normal cells (which are concentrated in the left area). Clearly, the addition of Ciclopirox is able to largely restore the normal HEK cellular phenotype in two different independent cell lines that produce the accumulation of UROI (HEK293 UROS-P248Q and HEK293 UROS-C73R).

Figure 5:
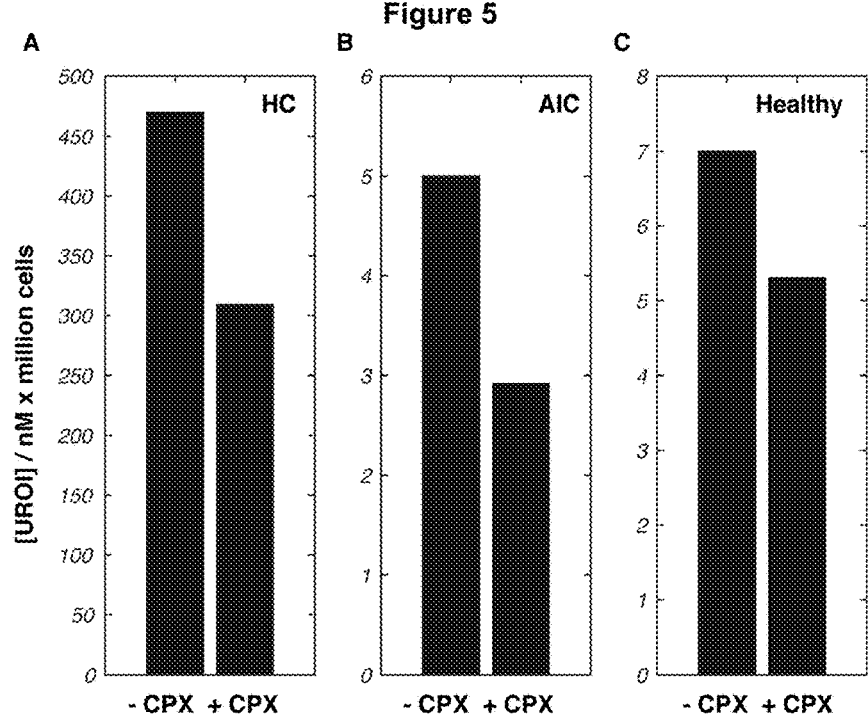
FIG. 5. Reduction levels of Uroporphyrin I (UROI) in a set of cell lines including: A) fibroblasts from an HC patient, B) fibroblasts from an AIP patient and C) fibroblasts from a healthy individual. In all cases a reduction of the UROI levels is observed in the presence of an extracellular concentration of CPX (15 µM).

3. Ciclopirox Reduces UROI Levels in Different Cellular Lines from Porphyria Patients:

Cell lines from different patients (fibroblasts) were amplified and incubated in the presence of CPX (15 µM). In all cases, a reduction of the UROI was observed as compared to an equivalent untreated cellular culture (FIG. 5), indicating that CPX effectively regulates porphyrins in disparate heme group metabolisms.

Figure 6:
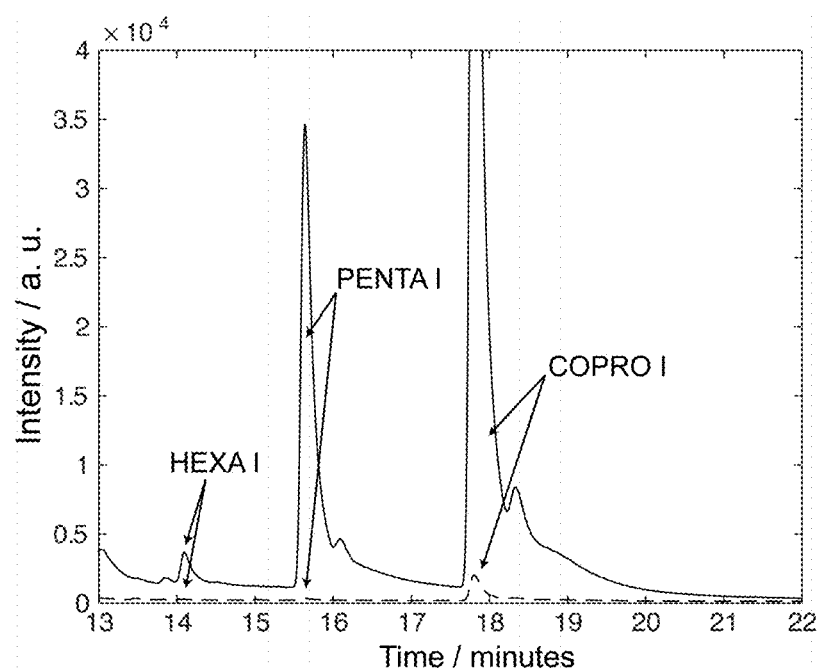
FIG. 6. Reduction levels of other porphyrines and derivatives. HPLC separation of penta I, hexa I and copro I as indicated for HEK-P248Q cells (solid line) and the same cells treated with 120 µM of CPX (dashed line).

4. Ciclopirox is Able to Modulate the Levels of COPROI and Other Porphyrines as Well FIG. 6 shows the HPLC chromatogram of HEK cells in the absence and in the presence of ciclopirox were clearly a reduction in certain porphyrines like hexa I, penta I and coprol can be appreciated. Similarly, the levels of bilirrubin and biliverdin can be monitored by the same analysis, simultaneously monitoring at 365 and 405 nm.

Figure 7:
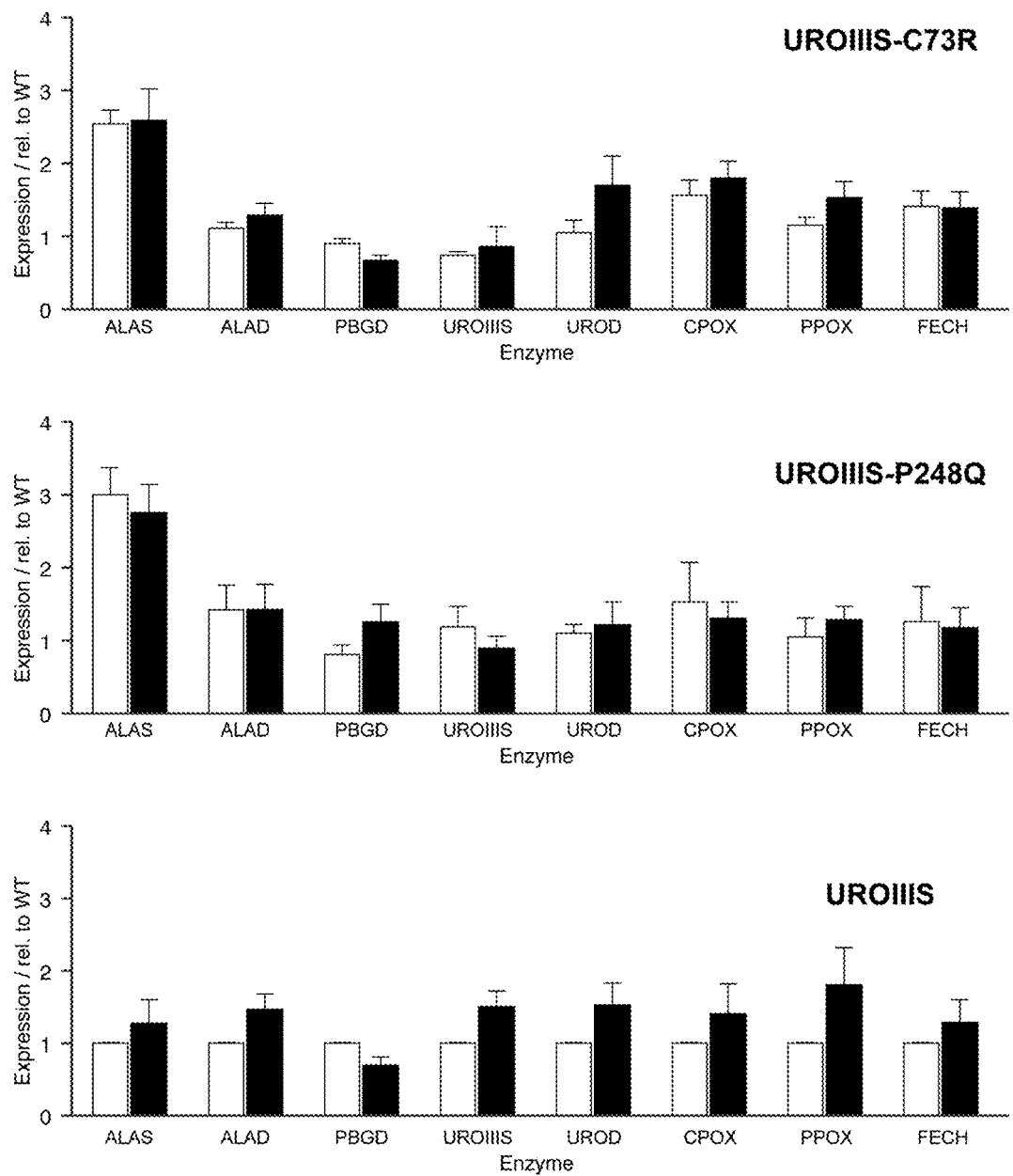
FIG. 7. Transcriptomic analysis of HEK cells (WT, UROIIIS-C73R and UROIIIS-P248Q as indicated) for the different genes of the heme biosynthetic pathway in the absence (white) and in the presence (black) of 120 µM CPX. Tubulin, actin and the ribosomal protein S14 have been used as housekeeping genes for quantification.

5. Ciclopirox does not Alter the Gene Regulation of the Heme Biosynthetic Pathway FIG. 7 shows the transcriptomic analysis of HEK cells (WT, UROIIIS-C73R and UROIIIS-P248Q as indicated) for the different genes of the heme biosynthetic pathway in the absence (white) and in the presence (black) of 120 µM CPX. The main difference observed is the upregulation of the ALAS gene for the cellular models of disease, as previously reported, but ciclopirox is not altering the gene expression for any of the enzymes in the pathway, thus indicating that the mechanism of action is not related to gene regulation.

Materials and Methods

In vitro cellular model of CEP: 50.000 K562 URO mutant cells/well are incubated in 250 µL of medium/well (RPMI media with 10% FBS). On the third day, the media is changed and the compound added in different concentration. The compound is incubated for 16-18 h at 37°. Finally, the effect of the compound is checked by fluorescence microscopy and by flow cytometry (FACS).

Other cellular models: Three additional cellular models were obtained from the Coriell Institute repository from different porphyria patients. The AIP line (Acute Intermittent Porphyria) corresponds to fibroblasts from a female carrying the T35M mutation. The HC (Hereditary Coproporphyria) and the healthy cell lines are fibroblasts from male individuals.

High performance liquid chromatography (HPLC): HPLC was used to separate and quantify porphyrins from PBGD and UROIIIS-C73N enzymatic assays and from cellular extracts. HPLC was carried out on a ODS Hypersil C18 column (5 um, 3×200 mm; Thermo Scientific, Mass., USA). Porphyrins were separated with a 15 min isocratic elution in a mobile phase of 89% 1M ammonium acetate buffer pH 5.16 and 11% Acetonitrile, at a flow rate of 0.5 mL/min, and were detected by fluorescence with an excitation wavelength 405 nm and emission wavelength 610 nm, which is characteristic of porphyrins. The sample injection volume was 20 µL.

NMR experiments. CPX-Heme binding constant was determined by collecting $^1$H-NMR spectra using zgpr pulse sequence in an Advance III NMR 800 MHz spectrometer. Taking 500 µM of Heme group as a constant value we prepared different titration points at 0, 0.2, 0.4, 0.6, 0.8, 1, 1.2, 1.4, 1.6, 1.8, 2, 2.5 and 5 Heme:CPX molar ratios using deuterated dimethyl sulfoxide (DMSO-D6) as a solvent. 200 µM of 4,4-dimethyl-4-silapentane-1-sulfonic acid (DSS) was added to each sample as a calibration standard. Spectra were processed and analyzed using TOPSPIN 3.2 software (BRUKER). Due to the unpaired electrons of Fe(II) that can interact with the protons close to this metal and broaden them (fast relaxation), observation of broadening in the specific signals of CPX is consequence of a direct interaction. CPX line broadening (signal disappearance) upon Heme addition was monitored using two specific peaks at 6.2 and 5.96 ppm. Peak areas were calculated and normalized using DSS. Further data analysis and $k_D$ stimation was perform using MATLAB in house scripts.

REFERENCES

Blouin J M, et al. *Proc. Natl. Acad. Sci. USA.,* 2013, 110, 18238-18243.

The invention claimed is:

1. Method for the treatment of a disease caused by dysregulated heme group biosynthesis in a subject and characterized by the accumulation of uroporphyrin I (UROI), coproporphyrin (COPROI), bilirubin and/or biliverdin, with the proviso that said disease is not congenital erythropoietic porphyria, said method comprising the administration of a therapeutically effective amount of ciclopirox, or a pharmaceutically acceptable salt or solvate thereof to said subject.

2. The method according to claim 1, wherein the salt is ciclopirox olamine.

3. The method according to claim 1, wherein the disease is a porphyria selected from the group consisting of sideroblastic anaemia, porphyria cutanea tarda, hereditary coproporphyria, harderoporphyria, variegate porphyria and erythropoietic protoporphyria.

4. The method according to claim 1, wherein the disease is selected from the group consisting of Crigler-Najjar syndrome, Lucey-Driscoll syndrome, Gilbert syndrome, Rotor syndrome, Dubin-Johnson syndrome and other hereditary hyperbilirubinemias.

5. The method according to claim 2, wherein the disease is a porphyria selected from the group consisting of sideroblastic anaemia, porphyria cutanea tarda, hereditary coproporphyria, harderoporphyria, variegate porphyria and erythropoietic protoporphyria.

6. The method according to claim 2, wherein the disease is selected from the group consisting of Crigler-Najjar syndrome, Lucey-Driscoll syndrome, Gilbert syndrome, Rotor syndrome, Dubin-Johnson syndrome and other hereditary hyperbilirubinemias.

7. Method for the treatment of a disease caused by dysregulated heme group biosynthesis in a subject and characterized by the accumulation of uroporphyrin I (UROI), coproporphyrin (COPROI), bilirubin and/or biliverdin, with the proviso that said disease is not congenital erythropoietic porphyria, said method comprising the administration to said subject of a pharmaceutical composition comprising a therapeutically effective amount of ciclopirox, or a pharmaceutically acceptable salt or solvate thereof and a pharmaceutically acceptable excipient.

8. The method according to claim 7, wherein said composition is for oral or topical administration.

9. The method according to claim 7, wherein said composition is selected from the group consisting of a lacquer, a shampoo, a solution, a suspension, a cream, a lotion or a gel.

10. The method according to claim 8, wherein said composition is selected from the group consisting of a lacquer, a shampoo, a solution, a suspension, a cream, a lotion or a gel.

11. The method according to claim 7, wherein the disease is a porphyria selected from the group consisting of sideroblastic anaemia, porphyria cutanea tarda, hereditary coproporphyria, harderoporphyria, variegate porphyria and erythropoietic protoporphyria; or a disease selected from the group consisting of Crigler-Najjar syndrome, Lucey-Driscoll syndrome, Gilbert syndrome, Rotor syndrome, Dubin-Johnson syndrome and other hereditary hyperbilirubinemias.

12. The method according to claim 8, wherein the disease is a porphyria selected from the group consisting of sideroblastic anaemia, porphyria cutanea tarda, hereditary coproporphyria, harderoporphyria, variegate porphyria and erythropoietic protoporphyria; or a disease selected from the group consisting of Crigler-Najjar syndrome, Lucey-Driscoll syndrome, Gilbert syndrome, Rotor syndrome, Dubin-Johnson syndrome and other hereditary hyperbilirubinemias.

13. The method according to claim 9, wherein the disease is a porphyria selected from the group consisting of sideroblastic anaemia, porphyria cutanea tarda, hereditary coproporphyria, harderoporphyria, variegate porphyria and erythropoietic protoporphyria; or a disease selected from the group consisting of Crigler-Najjar syndrome, Lucey-Driscoll syndrome, Gilbert syndrome, Rotor syndrome, Dubin-Johnson syndrome and other hereditary hyperbilirubinemias.

14. The method according to claim 10, wherein the disease is a porphyria selected from the group consisting of sideroblastic anaemia, porphyria cutanea tarda, hereditary coproporphyria, harderoporphyria, variegate porphyria and erythropoietic protoporphyria; or a disease selected from the group consisting of Crigler-Najjar syndrome, Lucey-Driscoll syndrome, Gilbert syndrome, Rotor syndrome, Dubin-Johnson syndrome and other hereditary hyperbilirubinemias.

* * * * *